US008871487B2

(12) United States Patent
Stinchcomb et al.

(10) Patent No.: US 8,871,487 B2
(45) Date of Patent: Oct. 28, 2014

(54) COMPOSITIONS, METHODS AND USES FOR INDUCING VIRAL GROWTH

(75) Inventors: Dan T. Stinchcomb, Fort Collins, CO (US); Jill A. Livengood, Fort Collins, CO (US); O'Neil Wiggan, Fort Collins, CO (US); Richard Kinney, Fort Collins, CO (US); Jorge Osorio, Mount Horeb, WI (US)

(73) Assignee: Takeda Vaccines, Inc., Deerfield, IL (US)

( * ) Notice: Subject to any disclaimer, the term of this patent is extended or adjusted under 35 U.S.C. 154(b) by 421 days.

(21) Appl. No.: 12/631,629

(22) Filed: Dec. 4, 2009

(65) Prior Publication Data

US 2010/0144015 A1 Jun. 10, 2010

Related U.S. Application Data

(60) Provisional application No. 61/120,262, filed on Dec. 5, 2008.

(51) Int. Cl.
*C12N 7/00* (2006.01)
*A61K 39/12* (2006.01)

(52) U.S. Cl.
CPC ........ *C12N 7/00* (2013.01); *C12N 2770/24151* (2013.01)
USPC .................................... 435/235.1; 424/218.1

(58) Field of Classification Search
None
See application file for complete search history.

(56) References Cited

U.S. PATENT DOCUMENTS

| | | | |
|---|---|---|---|
| 7,094,411 B2 * | 8/2006 | Kinney et al. ............... | 424/218.1 |
| 8,084,039 B2 * | 12/2011 | Stinchcomb et al. ...... | 424/204.1 |
| 2006/0148074 A1 | 7/2006 | Gorfein et al. | |
| 2008/0050770 A1 | 2/2008 | Zhang et al. | |
| 2008/0248551 A1 | 10/2008 | Stinchcomb et al. | |
| 2009/0203063 A1 * | 8/2009 | Wheeler et al. ................ | 435/29 |

OTHER PUBLICATIONS

International Search Report and Written Opinion of the International Searching Authority, PCT/US09/66848, Jan. 26, 2010.
Bhardwaj et al., "Controlled-Release Delivery System for the alpha-MSH Analog Melanotan-I Using Poloxamer 407," Journal of Pharmaceutical Sciences 1996, 85(9):915-919.
Burke et al., "Formulation, Stability, and Delivery of Live Attenuated Vaccines for Human Use," Critical Reviews in Therapeutic Drug Carrier Systems 1999, 16(1):1-83.
Coeshott et al., "Pluronic F127-based systemic vaccine delivery systems," Vaccine 2004, 22(19):2396-2405.
Desai et al., "Evaluation of Pluronic F127-Based Sustained-Release Ocular Delivery Systems for Pilocarpine Using the Albino Rabbit Eye Model," Journal of Pharmaceutical Sciences 1998, 87(10):1190-1195.
Johnston et al., "Sustained Delivery of Interleukin-2 from a Poloxamer 407 Gel Matrix Following Intraperitoneal Injection in Mice," Pharmaceutical Research 1992, 9(3):425-434.
Kabanov et al., "Pluronic block copolymers for overcoming drug resistance in cancer," Advanced Drug Delivery Reviews 2002, 54(5):759-779.
Katakam et al., "Use of Poloxamer Polymers to Stabilize Recombinant Human Growth Hormone Against Various Processing Stresses," Pharmaceutical Development and Technology 1997, 2(2):143-149.
Lee et al., "In Vivo Characterization of Sustained-Release Formulations of Human Growth Hormone," The Journal of Pharmacology and Experimental Therapeutics 1997, 281(3), 1431-1439.
Lemieux et al., "A combination of poloxamers increases gene expression of plasmid DNA in skeletal muscle," Gene Therapy 2000, 7(11), 986-991.
Melik-Nubarov et al., "Interaction of tumor and normal blood cells with ethylene oxide and propylene oxide block copolymers," FEBS Letters 1999 446(1):194-198.
Miyazaki et al., "Percutaneous absorption of Indomethacin from Pluronic F127 Gels in Rats," The Journal of Pharmacy and Pharmacology 1995 47(6):455-457.
Morikawa et al., "Enhancement of Therapeutic Effects of Recombinant Interleukin 2 on a Transplantable Rat Fibrosarcoma by the Use of a Sustained Release Vehicle, Pluronic Gel," Cancer Research 1987, 47(1):37-41.
Newman et al., "Design and Development of Adjuvant-Active Nonionic Block Copolymers," Journal of Pharmaceutical Sciences 1998, 87(11):1357-1362.
Paavola et al., "Controlled Release of Lidocaine from Injectable Gels and Efficacyt in Rat Sciatic Nerve Block," Pharmaceutical Research 1995, 12(12):1997-2002.
Strappe et al., "Delivery of a lentiviral vector in a Pluronic F127 gel to cells of the central nervous system," European Journal of Pharmaceutics and Biopharmaceutics 2005, 61(3):126-133.
Westerink et al., "ProJuvant (Pluronic F127/chitosan) enhances the immune response to intranasally administered tetanus toxoid," Vaccine 2002, 20:711-723.
Domachowske and Bonville, Overnight Titration of Human Respiratory Syncytial Virus Using Quatitative Shell Vial Amplification, BioTechniques, Oct. 1998, 25:644-647.
Lambeth, et al., Flow Cytometry-Based Assay for Titrating Dengue Virus, Journal of Clinical Microbiology, Jul. 2005, 43(7):3267-3272.

* cited by examiner

*Primary Examiner* — Stacy B Chen
(74) *Attorney, Agent, or Firm* — Faegre Baker Daniels, LLP

(57) ABSTRACT

Embodiments herein report methods, compositions and uses for inducing and/or accelerating viral growth. In certain embodiments, methods, compositions and uses generally related to copolymer compositions for inducing viral growth, reducing lag time and/or increasing viral plaque size. In other embodiments, methods, compositions and uses of copolymer compositions can be for inducing flaviviral growth, reducing lag in growth and/or increasing plaque size.

20 Claims, 5 Drawing Sheets

Fig. 5

Figure 1:
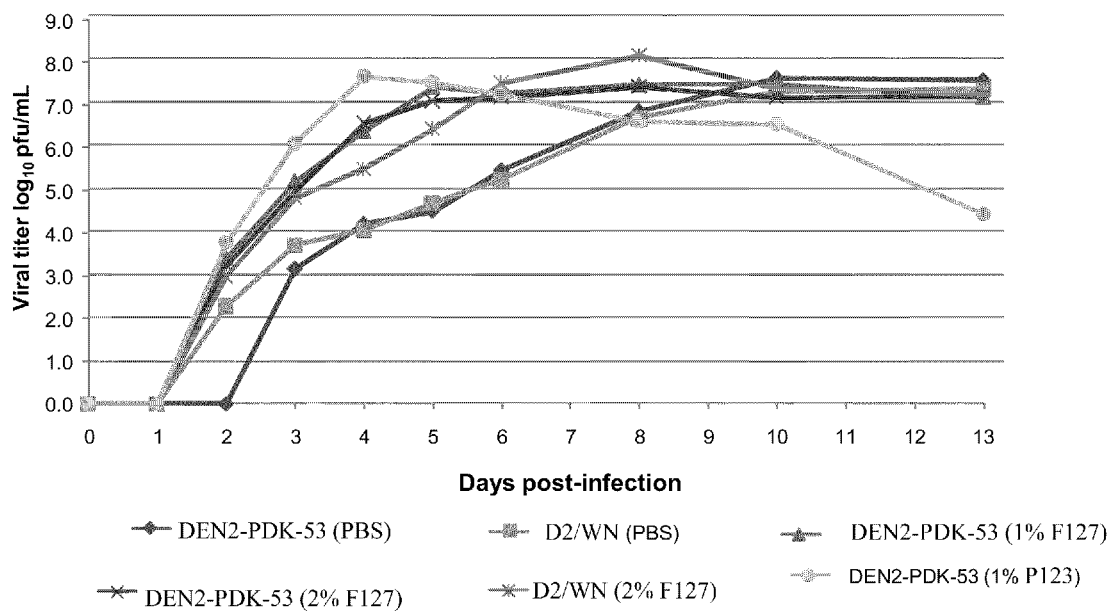
Figure 2:
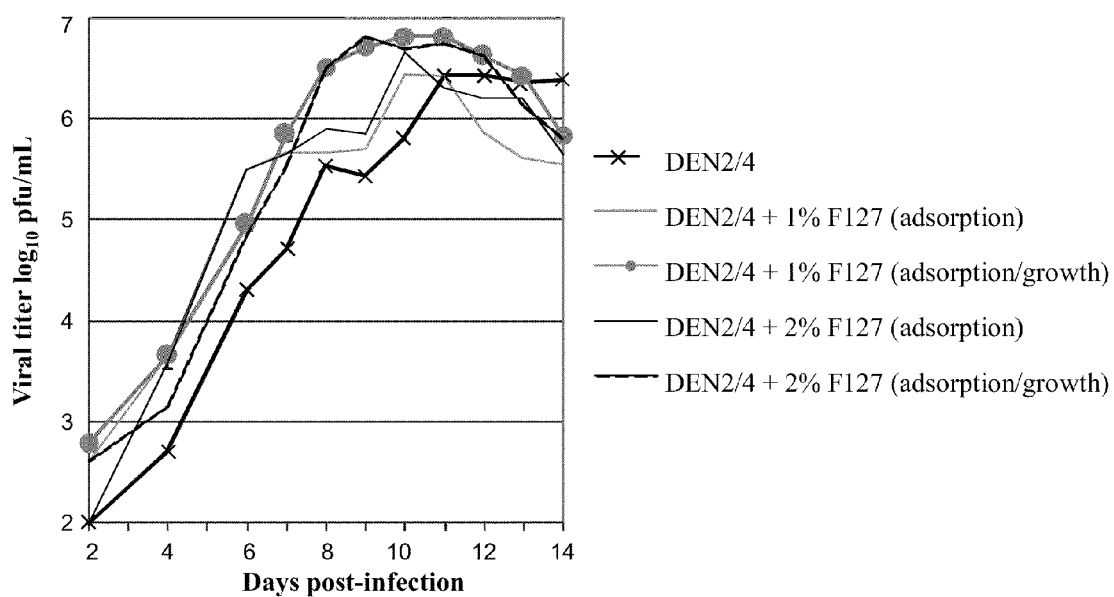
Figure 3:
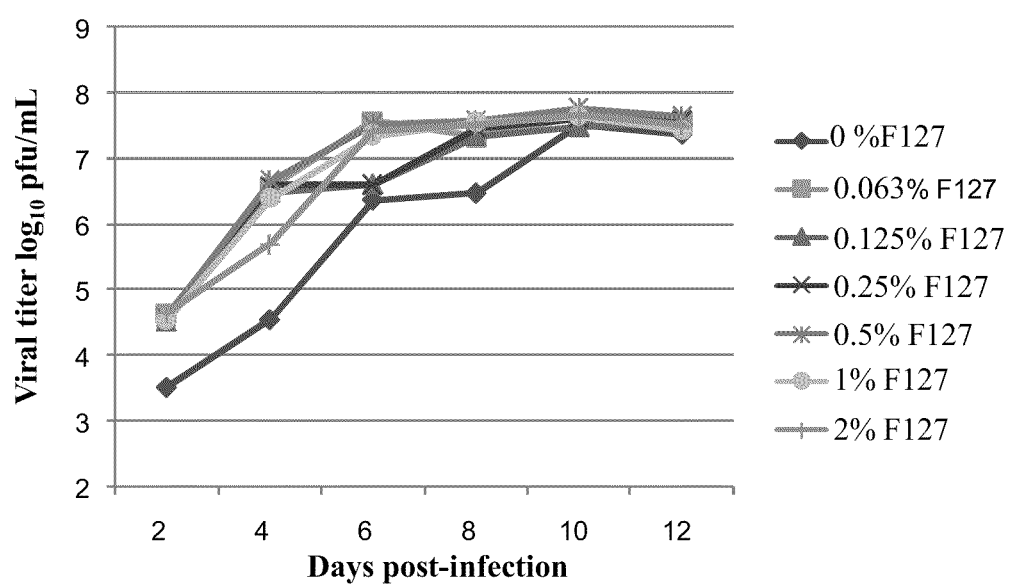
Figure 4:
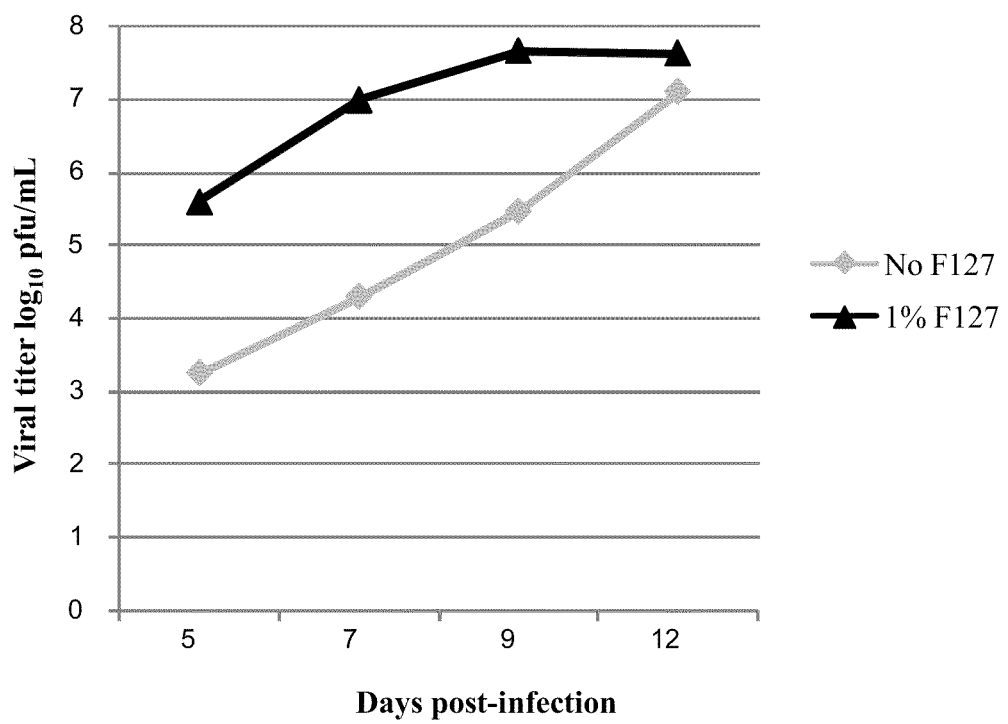

| F127 | Plaque Count | Sum (mm) | Average (mm) |
|---|---|---|---|
| 0% F127 | 8 | 56 | 7 |
| 0.1% F127 | 8 | 62 | 7.75 |
| 1% F127 | 8 | 70 | 8.75 |
| | | | |
| P-value = 0.019246 | | | |

COMPOSITIONS, METHODS AND USES FOR INDUCING VIRAL GROWTH

CROSS-REFERENCE TO RELATED APPLICATION

This application claims the benefit of U.S. Provisional Patent Application Ser. No. 61/120,262, filed on Dec. 5, 2008, and the provisional application is incorporated herein by reference in its entirety for all purposes.

FEDERALLY FUNDED RESEARCH

The studies disclosed herein were supported in part by grant numbers 5U01AI07443(-02/-03/-04) and 1U01AI070443-01 from the National Institutes of Health. The U.S. Government may have certain rights to practice the subject invention.

FIELD

Embodiments of this application generally report methods, compositions and uses for accelerated or enhanced viral growth. In certain embodiments, this application reports methods, compositions and uses of copolymer compositions for inducing accelerated viral growth and/or increasing viral plaque size. In other embodiments, methods, compositions and uses of copolymer compositions are reported for accelerating flaviviral growth, reducing flaviviral lag time and/or increasing flaviviral plaque size.

BACKGROUND

Vaccines to protect against infectious diseases have been used to improve human and animal health. One successful technology for viral vaccines is to immunize animals or humans with a weakened or attenuated strain of the virus (a "live, attenuated virus"). Due to limited replication after immunization, the attenuated strain does not cause disease. However, the limited viral replication is sufficient to express the full repertoire of viral antigens and generates potent and long-lasting immune responses to the virus. Thus, upon subsequent exposure to a pathogenic strain of the virus, the immunized individual is protected from disease.

Recent technical advances, such as reassortment, reverse genetics and cold adaptation, have led to advances of live, attenuated viruses for influenza and rotavirus. A number of live, viral vaccines developed with recombinant DNA technologies are in human clinical testing, including vaccines for West Nile disease, dengue fever, malaria, tuberculosis and HIV. These recombinant viral vaccines rely on manipulation of well-characterized attenuated viral vaccines, such as adenovirus, vaccinia virus, yellow fever 17D or the dengue virus, DEN-2 PDK-53. As a group, live attenuated viral vaccines are amongst the most successful medical interventions in human history, second only to the advent of antibiotics and hold the promise to improve public health throughout the world.

Other vaccines have been developed by inactivating viruses after growth in cell culture. These "killed virus" vaccines induce immune responses due to the presence of high concentrations of antigen present. Examples of effective killed viral vaccines include, but are not limited to, vaccine for rabies, influenza, hepatitis A, and poliovirus.

Flaviviruses cause a number of human and animal diseases of significant impact. They are enveloped viruses with a RNA genome of approximately 11,000 bases. Most of the flaviviruses are transmitted by an arthropod vector, commonly mosquitoes. There are over 70 different flaviviruses that are grouped into three major categories based on serology: the dengue group, the Japanese encephalitis group and the yellow fever group. Expanding urbanization, worldwide travel and environmental changes (such as deforestation or rain patterns) have lead to the emergence of several flaviviruses as threats to human public health. Such viruses include, but are not limited to, yellow fever virus, the dengue viruses, West Nile virus, Japanese encephalitis virus, and tick-borne encephalitis viruses.

Both live, attenuated viral vaccines and killed virus vaccines have been developed that are safe and protect against flavivirus diseases, for example, yellow fever and Japanese encephalitis.

SUMMARY

Embodiments of this application generally relate to methods, compositions and uses for inducing, enhancing and accelerating viral growth. In certain embodiments, this application reports methods, compositions and uses of copolymer compositions for inducing accelerated viral growth and/or increasing viral plaque size. In other embodiments, methods, compositions and uses of copolymer compositions are reported for accelerating flaviviral growth, reducing flaviviral lag time and/or increasing flaviviral plaque size.

One limitation for producing vaccines has been large-scale manufacture and in vitro growth of the viruses to support the demand of vaccines. Thus, one of the needs that exist in the art is for enhancing and accelerating viral growth. Certain embodiments of the present invention concern methods and compositions for enhancing and accelerating viral growth. These compositions are of use, for example, in production of viral vaccines and viral byproducts of use in other technologies such as manufacturing of viral-related gene therapies and other viral products. In addition, embodiments herein may be of use to enhance or accelerate growth of viral cultures of use in killed virus vaccines.

Certain compositions disclosed herein can include copolymers alone or in combination with other agents or compounds for enhancing and accelerating viral growth. Other embodiments herein concern combinations of excipients that enhance growth of live attenuated viruses. Copolymers of use herein include, but are not limited to, Pluronic® F127 (poloxamer 407), Pluronic® F68 (poloxamer 188), Pluronic® P123 (poloxamer 403), Pluronic® P85(poloxamer 235), other polyethylene oxide-polypropylene oxide (EO-PO) block copolymers of greater than 3,000-4,000 MW or combinations thereof.

In accordance with these embodiments, viruses can include, but are not limited to, Flavivirus, Togavirus, Coronavirus, Rhabdovirus, Filovirus, Paramyxovirus, Orthomyxovirus, Bunyavirus, Arenavirus, Retrovirus, Hepadnavirus, Pestivirus, Picornavirus, Calicivirus, Reovirus, Parvovirus, Papovavirus, Adenovirus, Herpes virus, and Poxvirus. Some embodiments, directed to compositions of use in viral cultures, can include, but are not limited to, cultures having one or more viruses, such as a mixture of viral species or a single species, or one or more live, attenuated viruses grown in one or more copolymer compositions alone, or in combination with other agents.

In other embodiments, compositions contemplated herein can increase plaque size in a reduced or similar time period of growth, compared to a control culture without the disclosed composition, for use in tittering, manufacturing or measuring the activity of virus preparations. In some aspects of the present invention, higher viral titers may be obtained in reduced time periods. Alternatively, compositions contemplated herein can reduce lag time or accelerate growth time up to several days compared to control viral cultures not using compositions contemplated herein.

Other embodiments concern virus populations for use in formulations and methods directed to vaccine formulations capable of reducing or preventing onset of a medical condition caused by one or more of the viruses contemplated herein. In accordance with these embodiments, medical conditions may include, but are not limited to conditions and/or infections including West Nile, dengue fever, Japanese encephalitis, Kyasanur forest disease, Murray valley encephalitis in Australia and New Guinea, Kunjin virus (a relative of West Nile), Alkhurma hemorrhagic fever, St. Louis encephalitis, hepatitis C virus infection, tick-borne encephalitis, yellow fever, the Usutu, Koutango, Yaonde viruses in Africa, and Cacipacore in South America. In certain embodiments, production time for generating vaccine formulations may be reduced by using compositions contemplated herein for accelerating viral growth production and manufacture, reducing lag time and/or increasing plague size of viral populations.

In certain embodiments, viral cultures contemplated for production herein may be used in compositions including, but not limited to, partially or wholly dehydrated or hydrated vaccine formulations or other viral formulations.

In certain embodiments, a live attenuated virus for use in a vaccine composition contemplated herein may include, but is not limited to, one or more live, attenuated flavivirus vaccines, including but not limited to, attenuated yellow fever viruses (e.g. 17D), attenuated Japanese encephalitis viruses, (e.g. SA 14-14-2), attenuated dengue viruses (e.g. DEN-2/PDK-53 or DEN-4Δ30), attenuated chimeric West Nile vaccines, or recombinant chimeric flaviviruses.

Other embodiments concern kits for growing viral cultures contemplated herein. It is contemplated that a kit may include partially or wholly dehydrated viral cultures of use in generating live, attenuated virus populations for vaccine production or other viral composition uses. It is also contemplated that a kit may include one or more growth inducing compositions disclosed herein.

BRIEF DESCRIPTION OF THE DRAWINGS

The following drawings form part of the present specification and are included to further demonstrate certain embodiments herein. The embodiments may be better understood by reference to one or more of these drawings alone or in combination with the detailed description of specific embodiments presented.

FIG. 1 represents an exemplary graph of Pluronic® F127 (poloxamer 407), effects on viral growth after cellular infection and introduction of a control agent or copolymer composition during viral adsorption.

FIG. 2 represents an exemplary graph illustrating growth of viral cultures in the presence of a copolymer during viral adsorption and/or growth.

FIG. 3 represents an exemplary graph illustrating growth of viral cultures in the presence of increasing amounts of a copolymer-containing composition during viral adsorption and growth.

FIG. 4 represents an exemplary graph illustrating growth of viral cultures in the presence or absence of a specific copolymer added during viral adsorption.

FIG. 5 represents an exemplary table illustrating change in plague size of exemplary viral cultures in the presence or absence of various concentrations of copolymer.

DEFINITIONS

As used herein, "a" or "an" may mean one or more than one of an item.

As used herein, vessel can include, but is not limited to, test tube, mini- or microfuge tube, plate, tissue culture flask, cell factory, channel, vial, microtiter plate or container.

As used herein the specification, "subject" or "subjects" may include but are not limited mammals such as humans or mammals, domesticated or wild, for example dogs, cats, ferrets, rabbits, pigs, horses, cattle, or zoo animals.

As used herein, "about" can mean plus or minus ten percent.

As used herein, "high molecular weight surfactants" can mean a surface active, amphiphilic molecule greater than 1500 molecular weight.

As used herein, "EO-PO block copolymer" can mean a copolymer consisting of blocks of poly(ethylene oxide) and poly(propylene) oxide. In addition, as used herein, "Pluronic® " can mean EO-PO block copolymers in the EOx-POy-EOx. This configuration of EO-PO block copolymer is also referred to as "Poloxamer" or "Synperonic".

As used herein, "attenuated virus" can mean a virus that demonstrates reduced or no clinical signs of viral-related disease when administered to a subject such as a mammal (e.g. a human or an animal).

As used herein, "accelerate" can mean decreasing the lag time before virus production begins or increasing the rate of viral production such that higher concentrations of virus are produced in a shorter amount of time or such that plaque size is increased in some embodiments relative to a control.

As used herein, "killed virus vaccine" can mean a vaccine prepared by inactivating a virus by any of a number of physical or chemical means known in the art.

Description

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Embodiments herein concern using various compositions to enhance growth rate or reduce lag time of viral growth in a culture. In accordance with these embodiments, compositions can include copolymer agents. Embodiments of this application generally relate to methods, compositions and uses for inducing and accelerating viral growth. In certain embodiments, this application relates generally to methods, compositions and uses of copolymer compositions for accelerating viral growth and/or increasing viral plaque size. In other embodiments, methods, compositions and uses of copolymer compositions for accelerating flaviviral growth, reducing lag in growth and/or increasing plaque size. Certain copolymer compositions contemplated herein include, but are not limited to, Pluronic® F127 (poloxamer 407), Pluronic® F68 (poloxamer 188), Pluronic® P85 (poloxamer 235), Pluronic® P123(poloxamer 403), other EO-PO block copolymers of greater than 3,000-4,000 MW or combinations thereof.

In certain embodiments, compositions can include copolymers, for example, Pluronic® F127 (poloxamer 407). Pluronic® F127 (poloxamer 407, also referred to herein as F127) is a non-ionic polyoxyethylene-poloxypropylene copolymer. Pluronic® block copolymers are known under their non-proprietary name as poloxamers. They were initially developed for use as surfactants. These compounds consist of hydrophilic ethylene oxide (EO) and hydrophobic propylene oxide (PO) blocks. The EO-PO block copolymers can include blocks of polyethylene oxide (—CH2CH2O— designated EO) and polypropylene oxide (—CH2CHCH3O— designated PO). The PO block can be flanked by two EO blocks in an EOx-POy-EOx arrangement. Since the PO component is hydrophilic and the EO component is hydrophobic, overall hydrophilicity, molecular weight and the surfactant properties can be adjusted by varying x and y in the EOx-POy-EOx block structure. According to the manufacturer, (e.g. BASF, Lutrol® F127) F127 can be used as a thickening agent and co-emulsifier in creams and liquid emulsions.

F127 undergoes a process known as reverse thermogelation, as it undergoes a phase transition from liquid to a gel upon reaching physiological temperatures. Higher temperatures promote the dehydration of an alkylene oxide unit of the block polymer and this can result in decreased solubility. Specifically, at high concentrations (for example: about 10% w/v) certain types of the higher molecular weight EO-PO block copolymers will undergo reverse gelation, forming a gel as the temperature increases. Additionally, when these block copolymers reside above the critical micelle concentration (CMC), they self assemble into micelles. In aqueous solutions, the EO-PO block copolymers will self-assemble into micelles with a PO core and a corona of hydrophilic EO groups. In certain studies, EO-PO block copolymer formulations have been investigated as potential drug delivery agents for a variety of hydrophobic drugs and for protein, DNA or inactivated vaccines.

The mechanism of activity of these Pluronic® block copolymers is currently unknown. Although, Pluronic® F127 (poloxamer 407) has been studied as a sustained release component of a vaccine delivery system in combination with chitosan. Vaccination of mice with Tetanus toxoid containing F127 increased the antibody response in intranasally delivered and systemically delivered tetanus antigens. In certain methods, Pluronics® have been shown to induce changes in the microviscosity and fluidity of cell membranes, which may contribute to its versatility.

Pluronic® F127 (poloxamer 407) has been used in a variety of human pharmaceutical applications including dental, oral and laxative pharmaceuticals. Vaccine formulations have also used surfactants as stabilizers to prevent material loss. Studies of DNA vaccine delivery with certain concentrations of F127 (0.01% w/v) have shown increased drug delivery, possibly by potentiating cellular uptake and recruitment of mature dendritic cells. Gel formation at body temperatures permits use of the EO—PO block copolymer gels to act as a drug depot in vaccine and drug delivery applications.

Certain compositions disclosed herein can include copolymers either alone or in combination with other agents or compounds. In addition, compositions disclosed herein may include a media composition having one or more copolymer agent(s) added to the media in addition to other media supplements. Medias of use in compositions disclosed herein may include any media known in the art known to grow viral organisms contemplated herein or a media specific for a particular viral organism. Other embodiments herein concern combinations of excipients that greatly enhance the growth of live viruses (e.g. attenuated viruses). Yet other compositions and methods herein are directed to reducing the lag time related to growth of viral organisms. Some embodiments concern modulating plague size of viral organisms. Copolymers of use herein include, but are not limited to, Pluronic® F127(poloxamer 407), Pluronic® F68 (poloxamer 188), Pluronic® P85 (poloxamer 235), Pluronic®P123 (poloxamer 403), other EO—PO block copolymers of greater than 3,000-4,000 MW or combinations thereof.

Compositions contemplated herein may be used alone or in combination with media before, during, and/or after viral cultures have been introduced to host culture cell media of compositions disclosed herein may be liquid, solid or semi-solid liquid. In certain embodiments, supplementary compositions may be added during entire viral growth periods in order to monitor, adjust or stimulate viral growth processes. In other embodiments, one or more supplementary copolymer compositions may be added to reduce lag time, accelerate viral growth and/or increase viral plaque size. Compositions contemplated herein may be used alone, in combination with other supplements (e.g. vitamins, metal ions and amino acids), or as a media supplement when media is added to the cultures.

Other embodiments include stocks for culturing viral cultures such as live attenuated virus including, but not limited to, Picornaviruses (e.g., polio virus, foot and mouth disease virus), Caliciviruses (e.g., SARS virus, feline infectious peritonitis virus), Togaviruses (e.g., sindbis virus, the equine encephalitis viruses, chikungunya virus, rubella virus, Ross River virus, bovine diarrhea virus, hog cholera virus), Flaviviruses (e.g., dengue virus, West Nile virus, yellow fever virus, Japanese encephalitis virus, St. Louis encephalitis virus, tick-borne encephalitis virus), Coronaviruses (e.g., human coronaviruses (common cold), swine gastroenteritis virus), Rhabdoviruses (e.g., rabies virus, vesicular stomatitis viruses), Filoviruses (e.g., Marburg virus, Ebola virus.), Paramyxoviruses (e.g., measles virus, canine distemper virus, mumps virus, parainfluenza viruses, respiratory syncytial virus, Newcastle disease virus, rinderpest virus), Orthomyxoviruses (e.g., human influenza viruses, avian influenza viruses, equine influenza viruses), Bunyaviruses (e.g., hantavirus, LaCrosse virus, Rift Valley fever virus), Arenaviruses (e.g., Lassa virus, Machupo virus), Reoviruses (e.g., human reoviruses, human rotavirus), Birnaviruses (e.g., infectious bursal virus, fish pancreatic necrosis virus), Retroviruses (e.g., HIV 1, HIV 2, HTLV-1, HTLV-2, bovine leukemia virus, feline immunodeficiency virus, feline sarcoma virus, mouse mammary tumor virus), Hepadnaviruses (e.g., hepatitis B virus.), Parvoviruses (human parvovirus B, canine parvovirus, feline panleukopenia virus) Papovaviruses (e.g., human papillomaviruses, SV40, bovine papillomaviruses), Adenoviruses (e.g., human adenovirus, canine adenovirus, bovine adenovirus, porcine adenovirus), Herpes viruses (e.g., herpes simplex viruses, varicella-zoster virus, infectious bovine rhinotracheitis virus, human cytomegalovirus, human herpesvirus 6), and Poxviruses (e.g., vaccinia, fowlpoxviruses, raccoon poxvirus, skunkpox virus, monkeypoxvirus, cowpox virus, musculum contagiosum virus).

In accordance with these embodiments, certain live attenuated viruses include, but are not limited to, live, attenuated flaviviruses. Some embodiments, directed to compositions, can include, but are not limited to, one or more live, attenuated viruses, such as one or more live, attenuated flaviviruses grown in one or more copolymer compositions alone or in combination with other agents. In accordance with these embodiments, a flavivirus can include, but are not limited to, dengue virus, West Nile virus, yellow fever virus, Japanese encephalitis virus, St. Louis encephalitis virus, tick-borne encephalitis virus or other known flavivirus.

In other embodiments, compositions contemplated herein can increase plaque size in reduced or similar time periods of growth, compared to controls not grown compositions disclosed herein, for use in assessing viral activity or tittering viral preparations. Alternatively, compositions contemplated herein can reduce lag time or accelerate growth time for up to several days earlier than control viral cultures not using compositions contemplated herein. In certain embodiments, predetermined viral titers may occur several hours, a half a day, 1 day, 2 days, 3 days, 4 days or even up to 10 days earlier than virus preparations grown in other media known in the art or supplemental compositions furnished to cultures having no copolymer. Optimal viral titer of some embodiments may be about $1\times10^6$ pfu/mL to about $1\times10^8$ pfu/mL. In certain embodiments, a flaviviral titer may reach concentrations of about $1\times10^7$ pfu/mL in about 4 days in media containing F127, as compared to cultures grown in media without F127 which takes about 6 days.

Some embodiments herein concern compositions and methods for modulating time for growth of a viral culture to reach a predetermined concentration. In accordance with these embodiments, time for growth may be reduced by about 5%, about 10%, about 15%, about 20%, about 25%, about 30%, about 35%, about 40% and more. In various embodiments, a predetermined viral culture density may be accomplished in about 80%, or about 70%, or about 60% of time using compositions disclosed herein compared to other compositions known in the art.

In certain embodiments, viral cultures contemplated for production herein may be used in compositions including, but not limited to, partially or wholly dehydrated or hydrated vaccine formulations. In other embodiments, viral cultures contemplated herein for production of vaccine formulations can be cultured for reduced time and costs. In addition, production of these vaccine formulations can be reduced in labor, time and costs, for example, in times when an epidemic or outbreak of flaviviral-associated diseases occur and vaccine formulations are required in a short period of time.

In some embodiments, a live attenuated virus for use in a vaccine composition contemplated herein may include, but is not limited to, one or more live, attenuated flavivirus vaccines, including but not limited to, attenuated yellow fever viruses (such as 17D), attenuated Japanese encephalitis viruses, (such as SA 14-14-2), attenuated dengue viruses (such as DEN-2/PDK-53 or DEN-4Δ30), attenuated chimeric West Nile virus, or recombinant chimeric flaviviruses. In certain embodiments, the flaviviral cultures of use in a vaccine composition can be grown in media compositions having one or more copolymer disclosed herein.

Other embodiments concern virus populations of use in formulations and methods directed to vaccine formulations capable of reducing or preventing onset of a medical condition caused by one or more of the flaviviruses contemplated herein. In accordance with these embodiments, medical conditions may include, but are not limited to, West Nile infection, dengue fever, Japanese encephalitis, Kyasanur forest disease, Murray valley encephalitis, Alkhurma hemorrhagic fever, St. Louis encephalitis, tick-borne encephalitis, yellow fever and hepatitis C virus infection. Thus, production time for generating these formulations can be reduced using compositions contemplated herein for increasing growth, reducing lag time and/or increasing plague size of viral populations used in formulations disclosed.

Other embodiments concern virus compositions of use in therapeutic applications. Such uses may include, but are not limited to, gene therapy applications. Viruses used to deliver genes to cells in gene therapy applications include lentiviruses, adenoviruses, adeno-associated viruses, and herpesviruses. Other uses of virus compositions may include, but are not limited to, cancer virus therapies (e.g., "oncolytic" viruses) or cancer immunotherapies.

It is contemplated herein that any media used for growth of cell cultures (e.g. host cells) may be of use herein. For example, commonly used medias for cell cultures are contemplated. In accordance with these embodiments, media may include, but are not limited to DMEM (Dulbecco's Modified Eagle Medium, high glucose, with L-glutamine, with pyridoxine hydrochloride, without sodium pyruvate containing 3.7 g sodium bicarbonate per liter), MEM, BSS/YE-LAH, F-10 (Ham's), F-12, M-199, RPMI, Agars, LB Broth, and PBS- based medias. In addition, it is contemplated that cells may be cultured by any means known in the art. For example, cells may be grown in confluent layers, as suspensions, in multiple layers, in roller bottles, in wells or in tubes.

In certain embodiments, host cells can be used to culture viruses disclosed herein. Any cell known to host viruses disclosed herein is contemplated. Some host cells of use for growing viruses disclosed herein include, but are not limited to, Vero (African green monkey Vero cells), LLC-$MK_2$ cells, C6/36 mosquito cells or other cells known in the art.

Some embodiments of the present invention report compositions having one or more high molecular weight surfactants or copolymer compounds of use in methods for culturing various viral cultures where some compositions disclosed herein are capable of modulating various aspects of viral growth (e.g. larger plaque size, reduced lag phase) by about 10%, by about 15%, by about 20%, by about 25%, by about 30%, by about 35%, by about 40%, by about 45%, by about 50% or more, compared to compositions not having a copolymer composition.

Kits

Further embodiments concerns kits of use for methods and compositions described herein. Compositions including, but not limited to, copolymer compositions and live virus formulations may be provided in a kit. Kits can also include, but are not limited to, a suitable container, copolymer compositions, live virus compositions detailed herein and optionally, one or more additional agents such as other anti-viral agents, antifungal agents or anti-bacterial agents for example, to modulate growth of undesireable species.

The kits may further include a suitably aliquoted copolymer composition of use for viral cultures. In addition, compositions herein may be partially or wholly dehydrated or aqueous viral cultures and/or host cells for propagating the viruses as well as liquid or partially or wholly dehydrated medias. Kits contemplated herein may be stored at room temperatures, frozen or at refrigerated temperatures as disclosed herein depending on the particular formulations and components.

The container means of the kits will generally include at least one vial, test tube, flask, bottle, syringe or other container means, into which a composition may be placed, and preferably, suitably aliquoted. Where an additional component is provided, the kit will also generally contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained.

The following examples are included to demonstrate certain embodiments presented herein. It should be appreciated by those of skill in the art that the techniques disclosed in the examples which follow represent techniques discovered to function well in the practices disclosed herein, and thus can be considered for its practice. However, those of skill in the art should, in light of the present disclosure, appreciate that many changes can be made in the specific embodiments which are disclosed and still obtain a like or similar result without departing from the spirit and scope herein.

EXAMPLES

Example 1

In one exemplary method, represented in FIG. 1, Pluronic® P123 or F127(poloxamer 403 or 407, respectively) effects on flavivirus growth were examined in one exemplary cell line, Vero cells (African green monkey Vero cells). Vero cells were grown to confluency for example, in T-75 cm2 flasks 2 days prior to infection with flavivirus (as indicated) at an MOI of 0.001. Virus adsorption for 180 minutes was assessed in 2 mL PBS in the presence or absence of Pluronic® (P123 or F127 (poloxamer 403 or 407, respectively)). Control samples contained viral adsorption in PBS without a copolymer. Growth media (18 mL serum-free DMEM) was added after adsorption. Aliquots were taken daily, and titrated on Vero cell monolayers. Viral titers were measured as illustrated in FIG. 1.

In another example, illustrated in FIG. 2, growth of the chimeric flavivirus DEN-2/4 in Vero cells, without or with varying concentrations of copolymer, Pluoronic F127 was examined. Vero cells were grown to confluency for example, in T-75 cm2 flasks 2 days prior to infection with DEN-2/4 at an MOI of 0.001. Virus was adsorbed for 120 minutes in 2 mL DMEM with or without F127.Viral inoculums were rinsed from the cell monolayer with PBS followed by addition of 25 mL indicated growth medium containing 5% FBS with or without F127 and grown for 14 days. Aliquots were taken daily, and titrated on vero cell monolayers. Viral titers were measured as illustrated in FIG. 2.

Example 2

In another exemplary method, growth of DEN 2/4 (Dengue 2/4) chimera in Vero cells containing increasing amounts of F127 during adsorption and growth were examined (see for example, FIG. 3). A confluent monolayer of Vero cells grown in T75 cm2 flasks in 25 mL DMEM medium containing 10% FBS and control or increasing concentrations of F127. Exemplary F127 concentrations used in this experiment included 0.063%, 0.125%, 0.25%, 0.5%, 1.0% and 2.0% F127. The cells were infected with DEN2/4 at MOI =0.001. Parameters included adsorption for 1.5 hours in 1mL DMEM/F127. Aliquots were taken every other day, and titrated on Vero cell monolayers. Viral titers were measured as illustrated in FIG. 3.

In addition, another experiment analyzed effects of the copolymer F127 during viral adsorption of the chimeric flavivirus DEN2/1. In this example, DEN2/1 was adsorbed onto a confluent flask of Vero cells at an MOI of 0.001 for 90 minutes. Adsorption was performed in 1 mL of growth media (BA-1) with or without 1% F127. After viral adsorption, 20 mL DMEM containing 2% FBS and no F127 was added to the cultures. Aliquots were taken every other day and titrated on Vero cell monolayers. Viral titers can be measured as illustrated in FIG. 4.

Example 3

Another exemplary method analyzed whether or not plaque size increased in the presence of an exemplary copolymer, F127. FIG. 5 represents an exemplary table, Table 1. This experiment demonstrated that flavivirus plaque size increases in the presence of increasing concentrations of Pluronic® F127 (Poloxamer 407) during growth. Here, confluent monolayer of Vero cells were grown in T75cm2 flask in 20 mL DMEM2% FBS medium in the presence or absence of F127 where the Vero cells were infected with DEN2/4 at MOI =0.001. Adsorption was 1.5 hours and 1 mL DMEM in the presence (0.1% or 1.0%) or absence of F127. Plaques (e.g. 8) were visualized on a light box, and their diameter was measured. Table 1represents results of one way ANOVA of plaque size (mm) differences in DENVax 2/4 growth in the absence of F127 or presence of increasing concentrations of F127.

It is contemplated that any method known in the art can be used for any composition, method and/or uses described herein. In certain embodiments, it is contemplated that certain methods will be more suited for viral growth, for example materials and methods of use for flaviviral growth, than other methods. In other embodiments, it is contemplated that certain methods will be more suited for the growth of Dengue, than suited for other flaviviruses. The following provides a brief description as to the methods to grow a high-titer chimeric Dengue vaccine or any live-attenuated flavivirus in the presence of F127. Using T-75 cm2 flask, for example, Vero cells are seeded 2 days prior to viral infection/adsorption at a density of 5×10^6 cells per flask. This viral growth can be "scaled up" to include tissue culturing vessels ranging from T-25 cm2 to 10-stack cell factories. Virus is adsorbed onto a confluent monolayer of Vero cells 2 days after cell seeding in lmL DMEM containing F127 (0.1%). The culture vessels are incubated for 1.5 hours at 37° C. with rocking of the vessel every 10 minutes. After viral adsorption, the cell monolayers are washed three times with 10 mL PBS. Growth medium (10 mL DMEM pH=7.2, containing 3.7 g/L $NaHCO_3$ and 0.1% F127 with no FBS) is then added to the monolayers, and incubated with or without aeration at 37° C. for 4 days. On day 4 of viral growth, the growth medium is replaced, as done after viral adsorption. Starting at day 6, and until day 12, the infectious medium is completely removed from the growth chamber and centrifuged for clarification. This viral growth is stabilized, and stored at −80° C. until its titer can be examined by plaque assay on Vero cell monolayers. After daily harvests, the growth medium is replaced on the tissue culture vessels as done on day 4. Daily harvests continue until day 12. Daily harvests are individually titered on Vero cells, and high-titer harvests can be pooled to obtain a homogeneous sample. Often, the first day harvest (day 6) is not included, to avoid high levels of host-cell (Vero) DNA.

TABLE 1

Example of DMEM - F12: F-12 Nutrient Mixture (Ham), powder (21700) with L-glutamine Additives per 10 L: 11.76 g Sodium Bicarbonate, 100 ml Penicillin Streptomycin

| COMPONENTS | Mole. Weight | Conc. (mg/L) | Molarity (mm) |
|---|---|---|---|
| INORGANIC SALTS: | | | |
| Calcium chloride (Anhydrous) | 111 | 33.22 | 0.299 |
| Cupric sulfate (CuSO4—5H2O) | 250 | 0.0025 | 0.00001 |
| Ferric sulfate (FeSO4—7H2O) | 278 | 0.834 | 0.003 |
| Potassium chloride (KCl) | 75 | 223.60 | 2.98 |
| Magnesium chloride (Anhydrous) | 95 | 57.22 | 0.60 |
| Sodium chloride (NaCl) | 58 | 7599.00 | 131.00 |
| Sodium bicarbonate (NaHCO3) | 84 | 1176.00 | 14.00 |
| Sodium phosphate, dibas (Anhydrous) | 142 | 142.00 | 1.00 |
| Zinc sulfate (ZnSO4—7H2O) | 288 | 0.863 | 0.003 |

TABLE 1-continued Example of DMEM - F12: F-12 Nutrient Mixture (Ham), powder (21700) with L-glutamine Additives per 10 L: 11.76 g Sodium Bicarbonate, 100 ml Penicillin Streptomycin

| COMPONENTS | Mole. Weight | Conc. (mg/L) | Molarity (mm) |
|---|---|---|---|
| OTHER COMPOUNDS: | | | |
| D-Glucose | 180 | 1802.00 | 1.00 |
| Hypoxanthine Na | 159 | 4.77 | 0.03 |
| Linoleic Acid | 280 | 0.084 | 0.0003 |
| Lipoic Acid | 206 | 0.21 | 0.000971 |
| Phenol red | 398 | 1.20 | 0.003 |
| Putrescine-2HCl | 161 | 0.161 | 0.001 |
| Sodium Pyruvate | 110 | 110.00 | 1.00 |
| Thymidine | 242 | 0.70 | 0.003 |
| AMINO ACIDS: | | | |
| L-Alanine | 89 | 8.90 | 0.100 |
| L-Arginine hydrochloride | 211 | 211.00 | 1.00 |
| L-Asparagine-H2O | 150 | 15.01 | 0.100 |
| L-Aspartic acid | 133 | 13.30 | 0.100 |
| L-Cysteine-HCl—H2O | 176 | 35.12 | 0.200 |
| L-Glutamic acid | 147 | 14.70 | 0.100 |
| L-Glutamine | 146 | 146.00 | 1.00 |
| Glycine | 75 | 7.50 | 0.100 |
| L-Histidine-HCl—H2O | 210 | 21.00 | 0.0998 |
| L-Isoleucine | 131 | 4.00 | 0.030 |
| L-Leucine | 131 | 13.10 | 0.100 |
| L-Lysine hydrochloride | 183 | 36.50 | 0.199 |
| L-Methionine | 149 | 4.50 | 0.030 |
| L-Phenylalanine | 165 | 5.00 | 0.030 |
| L-Proline | 115 | 34.50 | 0.300 |
| L-Serine | 105 | 10.50 | 0.100 |
| L-Threonine | 119 | 11.90 | 0.100 |
| L-Tryptophan | 204 | 2.04 | 0.010 |
| L-Tyrosine 2Na 2H2O | 225 | 7.81 | 0.03 |
| L-Valine | 117 | 11.70 | 0.100 |
| VITAMINS: | | | |
| Biotin | 244 | 0.0073 | 0.00003 |
| D-Calcium pantothenate | 477 | 0.50 | 0.001 |
| Choline chloride | 140 | 14.00 | 0.0997 |
| Folic acid | 441 | 1.30 | 0.0029 |
| i-Inositol | 180 | 18.00 | 0.100 |
| Niacinamide | 122 | 0.036 | 0.0003 |
| Pyridoxine hydrochloride | 206 | 0.06 | 0.0003 |
| Riboflavin | 376 | 0.037 | 0.000101 |
| Thiamine hydrochloride | 337 | 0.30 | 0.001 |
| Vitamin B12 | 1,355 | 1.40 | 0.001 |

Adjust the pH to 7.2

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A composition for growing viral cultures comprising:
   one or more ethylene oxide propylene oxide (EO-PO) block copolymers, the EO-PO block copolymers comprise poloxamer 407, poloxamer 403 or a combination thereof wherein the concentration of EO-PO block copolymer is from 0.063% to 3.0%;
   a viral culture;
   a host cell; and
   a media for growing the viral cultures,
   wherein the EO-PO block copolymers accelerate growth of viral cultures.

2. The composition of claim 1, wherein the viral cultures are selected from the group consisting of Flavivirus, Togavirus, Coronavirus, Filovirus, Paramyxovirus, Orthomyxovirus, Bunyavirus, Arenavirus, Retrovirus, Hepadnavirus, Pestivirus, Herpes virus, and Poxvirus.

3. The composition of claim 1, wherein the viral cultures are Flavivirus cultures.

4. The composition of claim 1, wherein the viral cultures are Poxvirus cultures.

5. The composition of claim 1, wherein at least one of the one or more ethylene oxide propylene oxide (EO-PO) block copolymers comprises poloxamer 407 and the media comprises Dulbecco's Modified Eagle Medium (DMEM).

6. A method for increasing viral growth rate comprising, administering to a host cell culture infected with a virus, a composition comprising one or more ethylene oxide propylene oxide (EO-PO) block copolymers, the EO-PO block copolymers comprise poloxamer 407, poloxamer 403 or a combination thereof wherein the concentration of EO-PO block copolymer is from 0.063% to 3.0% and a viral growth media, wherein the composition increases viral growth rate in the culture.

7. A method for increasing viral growth rate comprising, administering a composition comprising one or more ethylene oxide propylene oxide (EO-PO) block copolymers to a host cell culture, before, during, or after viral infection of the host cell culture and increasing viral growth rate in the host cell culture, wherein the EO-PO block copolymers comprise poloxamer 407, poloxamer 403 or a combination thereof wherein the concentration of EO-PO block copolymer is from 0.063% to 3.0%.

8. A method for increasing plaque size of a viral culture comprising, administering to a host cell culture infected with a virus, a composition comprising one or more ethylene oxide propylene oxide (EO-PO) block copolymers wherein the composition increases viral plaque size in the host cell culture compared to a control viral culture without administering one or more ethylene oxide propylene oxide (EO-PO) block copolymers, wherein the EO-PO block copolymers comprise poloxamer 407, poloxamer 403 or a combination thereof wherein the concentration of EO-PO block copolymer is from 0.063% to 3.0%.

9. A method for reducing growth lag time of a viral culture comprising, administering to a host cell culture infected with a virus, a composition comprising one or more ethylene oxide propylene oxide (EO-PO) block copolymers wherein the composition reduces lag time of the viral cultures in the host cell culture compared to a control viral culture without administering one or more ethylene oxide propylene oxide (EO-PO) block copolymers, wherein the EO-PO block copolymers comprise poloxamer 407, poloxamer 403 or a combination thereof wherein the concentration of EO-PO block copolymer is from 0.063% to 3.0%.

10. The method of claim 9, wherein the viral cultures are selected from Flaviviral cultures.

11. The method of claim 9, wherein the viral cultures comprise viral cultures for generating live, attenuated viral vaccines.

12. The method of claim 9, wherein the reduction in lag time comprises at least a 10 percent reduction in lag time compared to viral cultures without one or more ethylene oxide propylene oxide (EO-PO) block copolymers.

13. A kit for culturing viruses comprising;
at least one container; and
a composition comprising the composition of claim 1.

14. The kit of claim 13, wherein the viral culture are one or more Flaviviruses.

15. The kit of claim 13, further comprising a host cell stock culture comprising Vero (African green monkey Vero cells), LLC-MK2 cells (monkey kidney cells), or C6/36 mosquito cells.

16. The composition of claim 1, wherein the virus comprises Flavivirus and the host cell culture comprises Vero (African green monkey Vero cells), LLC-MK2 cells (monkey kidney cells), or C6/36 mosquito cells.

17. A composition for growing viral cultures comprising:
an ethylene oxide propylene oxide (EO-PO) block copolymer comprising poloxamer 403, at a concentration range of 0.063% to 3.0%;
a viral culture;
a host cell; and
a media for growing the viral cultures,
wherein the EO-PO block copolymer induces growth of viral cultures, wherein the host cells are grown to confluence.

18. The composition of claim 17, further comprising-_poloxamer 407.

19. A composition for growing viral cultures comprising:

one or more ethylene oxide propylene oxide (EO-PO) block copolymers, the EO-PO block copolymers are selected from the group consisting of poloxamer 407, poloxamer 403, and a combination thereof wherein the concentration of EO-PO block copolymer is about 0.063% to 3.0%;

a viral culture;

a host cell; and a media for growing the viral cultures, wherein the EO-PO block copolymers accelerate growth of viral cultures, wherein the host cells are grown to confluence.

20. The composition of claim 19, wherein the viral culture titer is from about $1\times10^6$ pfu/mL to about $1\times10^9$ pfu/mL.

* * * * *

UNITED STATES PATENT AND TRADEMARK OFFICE
CERTIFICATE OF CORRECTION

PATENT NO. : 8,871,487 B2  
APPLICATION NO. : 12/631629  
DATED : October 28, 2014  
INVENTOR(S) : Dan T. Stinchcomb et al.

Page 1 of 1

It is certified that error appears in the above-identified patent and that said Letters Patent is hereby corrected as shown below:

On the Title Page, in the (57) Abstract:

Line 4, replace "related" with "relate".

In the Claims:

Claim 18, column 14, line 4, delete "-" before "_poloxamer 407".

Signed and Sealed this  
Fourteenth Day of April, 2015

Michelle K. Lee  
*Director of the United States Patent and Trademark Office*

UNITED STATES PATENT AND TRADEMARK OFFICE
CERTIFICATE OF CORRECTION

| | | |
|---|---|---|
| PATENT NO. | : 8,871,487 B2 | Page 1 of 1 |
| APPLICATION NO. | : 12/631629 | |
| DATED | : October 28, 2014 | |
| INVENTOR(S) | : Dan T. Stinchcomb et al. | |

It is certified that error appears in the above-identified patent and that said Letters Patent is hereby corrected as shown below:

In the Specification:

Replace paragraph [0002] of the application as filed under FEDERALLY FUNDED RESEARCH with the corrected paragraph below:

"This invention was made with Government support under U01 AI070443 awarded by the National Institutes of Health. The Government has certain rights in this invention."

Signed and Sealed this
First Day of September, 2015

Michelle K. Lee
*Director of the United States Patent and Trademark Office*